US008016743B2

(12) United States Patent
Romero Maroto

(10) Patent No.: US 8,016,743 B2
(45) Date of Patent: Sep. 13, 2011

(54) SYSTEM FOR THE TREATMENT OF STRESS URINARY INCONTINENCE

(76) Inventor: Jesus Romero Maroto, El Campello (ES)

( * ) Notice: Subject to any disclaimer, the term of this patent is extended or adjusted under 35 U.S.C. 154(b) by 831 days.

(21) Appl. No.: 12/047,168

(22) Filed: Mar. 12, 2008

(65) Prior Publication Data

US 2008/0210248 A1    Sep. 4, 2008

Related U.S. Application Data

(63) Continuation-in-part of application No. 10/515,770, filed as application No. PCT/ES03/00128 on Mar. 18, 2003, now abandoned.

(30) Foreign Application Priority Data

May 29, 2002 (ES) ................................ 200201227 U
Oct. 6, 2004 (ES) ................................ 200402270 U

(51) Int. Cl.
*A61F 2/02* (2006.01)
(52) U.S. Cl. ........................................... 600/30; 600/37
(58) Field of Classification Search .............. 600/29–30, 600/37; 128/DIG. 25; 606/222, 223, 151–158
See application file for complete search history.

(56) References Cited

U.S. PATENT DOCUMENTS

| 4,973,300 | A | 11/1990 | Wright |
| 6,042,534 | A | 3/2000 | Gellman et al. |
| 6,328,686 | B1 | 12/2001 | Kovac |
| 6,648,921 | B2 | 11/2003 | Anderson et al. |
| 2003/0050530 | A1 | 3/2003 | Neisz et al. |
| 2004/0054253 | A1 | 3/2004 | Snitkin et al. |

FOREIGN PATENT DOCUMENTS

| ES | 2 021 359 | 12/1987 |
| ES | 2 211 286 | 7/2004 |
| FR | 2 787 990 A1 | 7/2000 |
| FR | 2 814 939 A1 | 4/2002 |
| WO | WO 00/74633 A2 | 12/2000 |
| WO | WO 02/28313 A1 | 4/2002 |
| WO | WO 02/28314 A2 | 4/2002 |

*Primary Examiner* — John Lacyk
(74) *Attorney, Agent, or Firm* — Sughrue Mion, PLLC

(57) ABSTRACT

The inventive system includes an elongated band, which includes a urethral area at a central part of the band, the band including a first set of holes, one of the first set of holes located on one side of the central part and another of the first set of holes located on the other side of the central part along the length of the band, first threads passing through the first set of holes and configured to permit loosening of the band following the placement of the band and the conclusion of the operation, and a second set of holes located closer to distal ends of the band than the first set of holes, and second threads passing through the second set of holes and configured to permit tightening of the band following the placement of the band and the conclusion of the operation.

10 Claims, 5 Drawing Sheets

SYSTEM FOR THE TREATMENT OF STRESS URINARY INCONTINENCE

CROSS-REFERENCE TO RELATED PATENT APPLICATION

This is a continuation-in-part application claiming the benefit of International Application No. PCT/ES03/00128 filed on Mar. 18, 2003 which entered national stage in the U.S. on Nov. 24, 2004 now abandoned as U.S. application Ser. No. 10/515,770, and International Application No. PCT/ES2005/000419 filed on Jul. 26, 2005 which entered national stage in the U.S. on Apr. 4, 2007 as U.S. application Ser. No. 11/664,587, the disclosures of which are incorporated herein by reference in their entirety.

BACKGROUND OF THE INVENTION

1. Field of the Invention

The present invention relates to an improved system for the treatment of stress urinary incontinence, which provides essential characteristics of novelty and appreciable advantages in relation to the known methods and devices used for the same purposes in the related art.

2. Description of the Related Art

The fact that stress urinary incontinence is a frequent pathology in women is generally known, involving urine loss when abdominal stress is performed such as coughing, going from the sitting position to that of standing up or walking.

This problem is an illness which frequently causes a serious reduction in the quality of life, as a consequence of the voluntary limitation of multiple activities, due to fear and shame that this urine loss may be noted by other people, and which often leads to situations of loneliness and isolation.

The anatomic alteration that lies behind this urine loss symptomology induces the descent of the vesical neck and the urethra due to the alteration of the perineal muscles, and which can be caused, among other reasons, by giving birth. The descent of the vesical neck and urethra means that abdominal pressures are not correctly transmitted thereto, this set of altered pressures being the cause of the involuntary urine leaks.

Until now, some techniques have been proposed that tend to provide solutions to this problem. In any case, the solution to the problem of incontinence is surgical and involves returning the vesical neck and urethra to their original position, then providing them with a support that permits the correct transmission of abdominal pressures thereto. Amongst the techniques used, that known as the sling technique is the one which provides a more efficient, lasting solution.

This sling technique involves placing a tissue band, whether from the patient herself or heterologous tissue (marlex, silicone and, lately and with improved results, prolene), in a sub-cervical or sub-urethral position, so that once the band is fixed in different points according to the technique, it lifts and supports the vesical neck and the urethra in their original position, thus enabling pressure transmission and avoiding urine loss.

The tissue band can be sufficiently long to go from the urethra to the hypogastrium, or it can include only a small patch joined to several (e.g., four) threads, that are later attached to the abdominal wall.

The aggressiveness of the technique has been considerably reduced since it is performed intravaginally, without needing to open the pelvic cavity, and since prolene has been used, as it avoids having to collect aponeurosis from the same patient.

Recently, within the concept of this surgery as non-evasive, two sets have come onto the market for urinary incontinence surgery, identified by the acronyms TVT and SPARC. Both use a polypropylene mesh, surrounded by a plastic cover, and a connector system using a needle with a handle. Both techniques are differentiated in that, in the case of TVT, the needle is passed through the vagina towards the hypogastrium, needing to separate the urethra with a probe and a catch, whilst in the case of the SPARC technique, this step is performed in the direction of hypogastrium to the vagina, without the urethra needing to be separated by a probe. In both cases, the polypropylene mesh used, surrounded by a plastic cover, is passed through the vagina to the hypogastrium, which has facilitated the mesh passing through, leaving the latter positioned subcutaneously, where it is fixed due to the properties it has been provided with.

In both techniques, and all those wherein the sling system is used, an important problem is correctly adjusting the tension given to the sling, a special feature that conditions the success or failure of this type of surgery. Furthermore, if this sling is subjected to excessive tension, a urinary obstruction may occur, so that the patient will have difficulties in eliminating urine. In contrast, if sufficient tension is not provided, the patient will then continue to have an incontinence problem.

There is, therefore, a practical difficulty associated with the fact that there is no way of calculating the most appropriate tension, having to do so randomly and approximately. Once the operation has concluded, it is then not possible to correct the excess or lack of tension, which leads to a failure rate estimated at between 10% and 20% of the operations. Furthermore, this problem is the cause of all failures which occur with the application of this technique.

The existence of a system identified as REEMEX is also known in the market, wherein a subcutaneous implant of a device in the form of a pulley is performed in the hypogastrium, which permits, with the use of a screwdriver, and during the postoperative, to increase the tension given to a sling formed by a small patch of tissue fastened with four threads. This system is expensive, complex and suffers from considerable potential complications, due to the fact that it requires the implantation of a foreign body. It also can be loosened if the sling has been made with threads, but the system cannot be used when it uses a sling only formed from mesh, i.e. of TVT or SPARC type.

Finally, there is another system currently in existence, although there is no knowledge of its commercialization, consisting of a development by Dr. Gil Vernet, which includes a liquid reservoir implanted in subcutaneous tissue in the hypogastrium. The threads which fasten the sling have been attached to the reservoir. The system allows, if there is little tension, that the reservoir can be filled with liquid, thereby increasing the tension. The system is of equally difficult clinical application, and cannot be used with complete meshes.

Another technique that has recently appeared is TOT, which differs from the previous techniques in that the mesh is passed through the obturator foramen instead of the hypogastrium, with the same intention of returning the urethra and the bladder neck to their correct position. This technique presents the same difficulty of adjusting the exact tension of the mesh, which also results in a significant failure rate.

In accordance with the previous description, the systems used in the application of the sling technique have a series of drawbacks associated with their use, which do not permit the fully satisfactory use thereof.

SUMMARY OF THE INVENTION

The present invention has proposed the main objective of developing a system and method whereby an efficient, quick, economic solution is provided to these problems discussed above, especially that regarding the application of the sling system and technique.

This objective has been fully attained by the system of the invention and method of use thereof, wherein a mesh positioning device (or thread passer) and a mesh, intervene as fundamental elements.

According to an aspect of an embodiment of the present invention, there is provided a system for the treatment of stress urinary incontinence by returning the vesical neck and the urethra to a correct position with the use of a band positioned beneath the urethra and tightened to a desired position. The system includes a band positioning device, which includes a handle, a needle, and a hole at or near a distal end of the needle; and an elongated band, which includes a urethral area at a central part of the band. The band includes a first set of holes, one of the first set of holes located on one side of the central part and another of the first set of holes located on the other side of the central part along the length of the band, first threads passing through the first set of holes and configured to permit loosening of the band following the placement of the band and the conclusion of the operation, and a second set of holes located closer to distal ends of the band than the first set of holes, and second threads passing through the second set of holes and configured to permit tightening of the band following the placement of the band and the conclusion of the operation.

The first threads and the second threads may be structured and located so that, following the placement of the band on a aponeurosis of the rectus level and periurethral level and the conclusion of the operation, the first threads and the second threads are accessible outside the corresponding lines of vaginal and retropubic sutures for post-operative adjustment of the mesh.

The band may narrow at both ends, terminating in filiform elements configured to be threaded through the hole of the needle during the operation.

The hole in the needle may be an elongated hole extending in a longitudinal direction of the needle.

The band may have a mesh structure.

The center part of the band may be a urethral apposition area and one of the first set of holes may be positioned at a distance of approximately 1 and 2 cm from the center part of the band and the another of the first set of holes is positioned at a distance of approximately 1 and 2 cm from the center part of the band on an opposite side of the central part of the band.

The mesh and the first threads may be assembled and configured to permit loosening of the band following the placement of the band and the conclusion of the operation without the mesh first including folds prior to loosening.

The system may be constructed so as to provide post-operative adjustment of the mesh without folds in the mesh.

The adjustment may include loosening of the mesh constructed so as to provide post-operative adjustment of the mesh without folds in the mesh.

The needle of the band positioning device may have a smaller caliber than those currently known.

According to another aspect of the invention, there is provided a system for the treatment of stress urinary incontinence by returning the vesical neck and the urethra to a correct position with the use of a band positioned beneath the urethra and tightened to a desired position, including a band positioning device, which includes a handle, a needle, and a hole at or near a distal end of the needle, an elongated band, which includes a urethral area at a central part of the band, and means for loosening and tightening the band following the placement of the band and the conclusion of the operation.

The mechanism for loosening and tightening the band following the placement of the band and the conclusion of the operation may not involve folds in the mesh.

The band positioning device has the advantage that it is of smaller caliber than those currently used, meaning it is less aggressive, with a considerable reduction in the possibilities of causing iatrogenic lesions; furthermore, the thread passer is universal, i.e. it serves for both directions, being able to pass from vagina to hypogastrium, or from hypogastrium to vagina. Also, regarding the connection system of the mesh to the band positioning device, it has been considerably simplified, as a hole in the distal part of the needle permits threading the end part of the mesh formed by threads.

The mesh provided for this application is consistent with a view to maintain the vesical neck and the urethra in an optimum position. It has certain advantageous characteristics in comparison with those used at present, including, for example, the fact that it has no additional cover and requires no withdrawal or extraction period as occurs at present, thus simplifying the procedure. Furthermore, the mesh terminates in a reduction at the ends to two threads, which are those that are threaded in the thread passer and achieve the positioning of the mesh by pulling. Also, as another characteristic, since the mesh has holes distributed thereon, in predetermined positions, it can be tightened/loosened with a view to eliminating any obstruction or, respectively, correcting the incontinence. The adjustment (i.e., tightening/loosening) can be carried out once the mesh has been positioned on an aponeurosis of the rectus level and periurethral level, allowing threads to be introduced in said holes, whose ends are positioned, once the operation has concluded, outside the lines of vaginal and retropubic suture. If the incontinence persists even after the operation, the adjustment can be performed the day after the operation, with the patient awake, carrying out her typical activities, thus allowing any dysfunction caused from the sling implantation to be corrected, by acting on the vaginal or retropubic threads.

BRIEF DESCRIPTION OF THE DRAWINGS

The above and other features of the present invention will become more apparent by describing in detail non-limited exemplary preferred embodiments thereof with reference to the attached drawings in which.

DETAILED DESCRIPTION OF THE INVENTION

The present invention will now be described more fully with reference to the accompanying drawings, in which exemplary embodiments of the invention are shown.

Figures 1, 2:
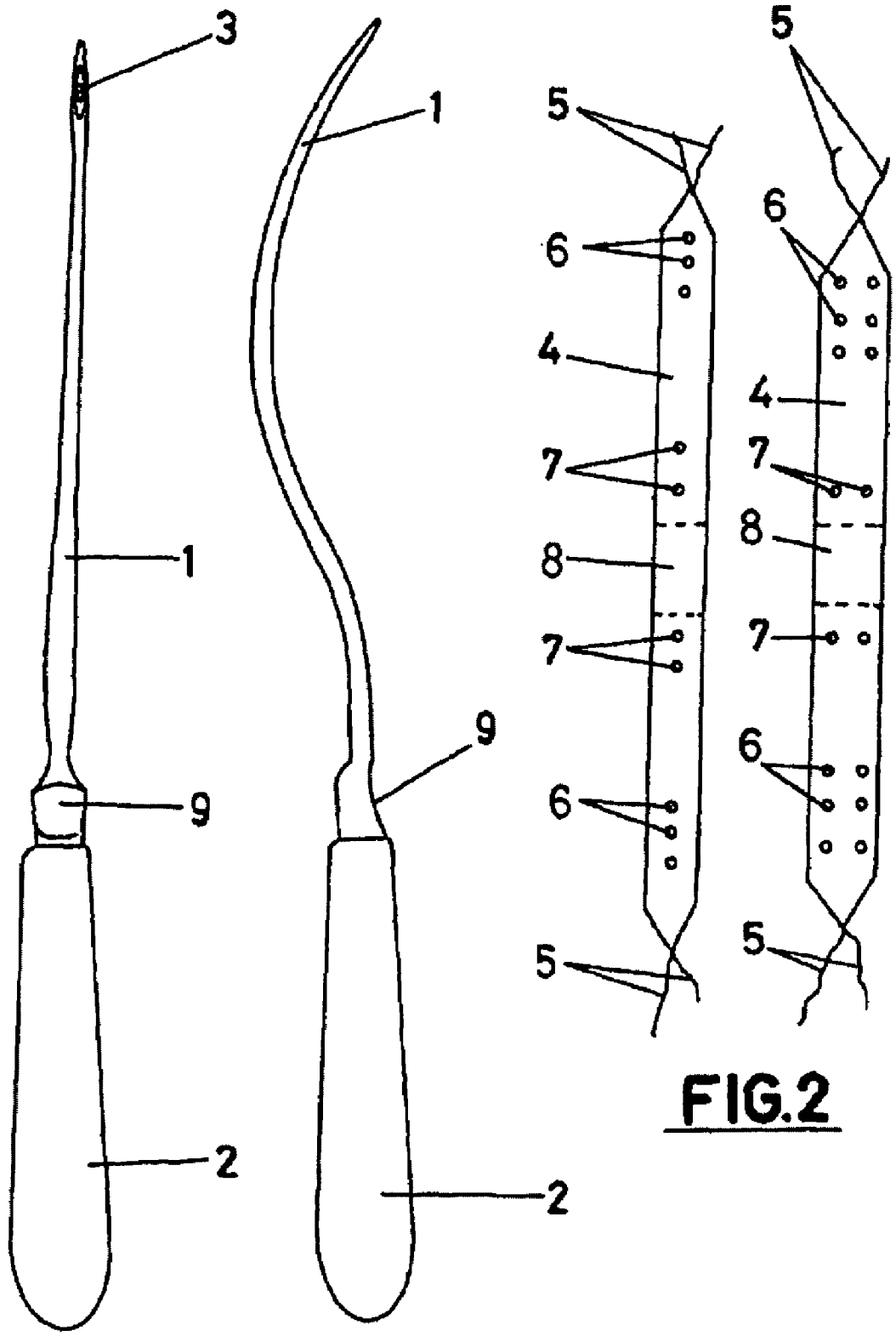
FIG. 1 shows side elevation and front elevation views of the mesh positioning element according to an exemplary embodiment of the present invention.
FIG. 2 is an illustrative representation of two alternative meshes, configured in accordance with alternative embodiments of the present invention.

FIG. 1 shows different views corresponding to the side elevation and front elevation views of a mesh positioning device (or thread passer), configured so that therein is a needle portion (tunneller) (1) and a handle portion (2). The needle portion (1), is elongated, with a predetermined length sufficient for the purpose for which it is intended, and it has been provided with a certain curve throughout, terminating in a blunt point at the distal end thereof. A through hole (3) has been provided in the proximity of this distal end, which is slightly elongated, coinciding with the longitudinal direction of the needle, and of considerable size, which can especially be observed in the front view of the positioning device. As will be understood, the positioning device can be constructed with the use of various materials that allow correct sterilization, such materials including both those of perishable and disposable type and reusable type.

Furthermore, the handle portion (2) is represented with a conventional form, ergonomically shaped to permit easy, comfortable gripping by the device user, provided with a depression (9) to support the thumb with a view to safer gripping, and of dimensions that facilitate the unit's handling.

FIG. 2 shows the schematic representation of a portion of mesh of the type used as support in the correct positioning of the vesical neck and urethra. The mesh portion is indicated by reference number (4), and has a band that, in its preferred embodiment, has an approximately rectangular shape whose ends are narrowed and converge to terminate in filiform elements (5) at each one of its ends, whilst, on areas positioned around each end and, where appropriate, in other intermediate areas, the mesh portion has been provided with several respective holes (6, 7).

In accordance with both alternative embodiments of the mesh shown in FIG. 2, the holes (6, 7) can be grouped in different forms, longitudinally or transversally, in rows and/or lines, depending on the number of holes made in accordance with the mesh width. This special feature can be easily observed in the examples illustrated in FIG. 2, wherein, in the first alternative or mesh with less width, there are sets of three holes (6) beside the ends arranged longitudinally in rows, and sets of two holes (7) at both sides of an intermediate area (8), or urethral area, whilst in the second alternative or mesh with greatest width, there are sets of six holes beside both ends, arranged in two parallel rows of three holes each, whilst on both sides of the urethral area (8), two transversally aligned holes have been represented. Of course, as we have mentioned, the arrangement can be any other.

As will be understood, the inclusion of these holes (6, 7), permits the positioning device (1) to be applied with a view to pulling from any position, or even passing threads (not represented) through one or more of the holes, to be able to be then threaded through the hole (3) of the positioning device, and to be able to suitably adjust the positioning of the urethra which, in short, is an aim sought.

Preferably, two of the holes (7) of the mesh, are arranged at approximately 1 and 2 cm from the urethral apposition area (8), whilst the other holes are arranged starting approximately five centimeters from the urethral area. The threads that pass through the holes (6), will be, once the operation has finished, positioned outside the vaginal and retropubic suture lines. As previously mentioned, by acting on the vaginal and retropubic lines, one can adjust the tension of the mesh to the most suitable tension for the patient's pathological characteristics. Furthermore, this form of mesh used by the system of the invention, also permits that the threads (5), projected from each end of the mesh (4), can be threaded in the hole (3) of the positioning device, so that it can be taken to its correct position.

Figure 3:
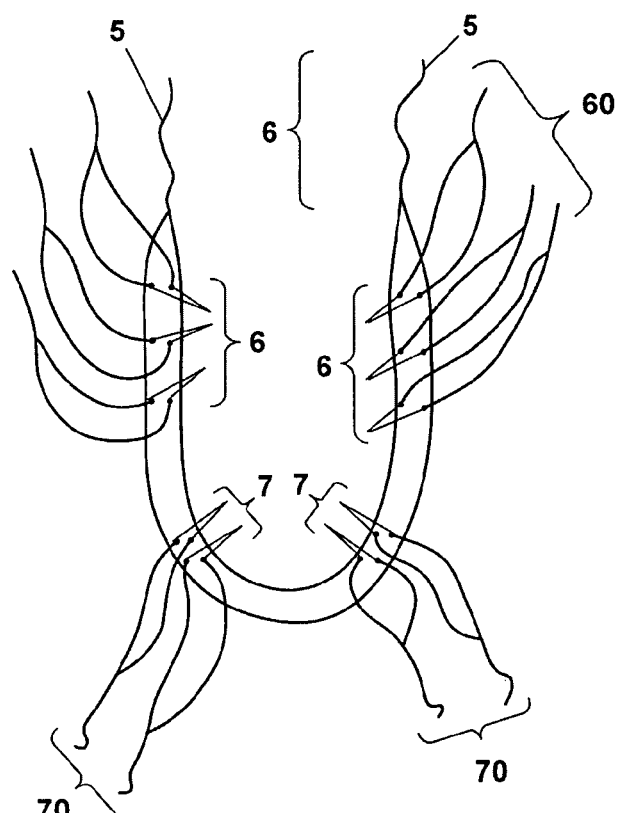
FIG. 3 is an illustrative representation of an elongated band with a first set of holes and corresponding first threads for loosening the band and a second set of holes and corresponding second threads for tightening the band.

Referring to FIG. 3, the elongated band 4, whose central part 8 is referred as the urethral area 8, includes two sets of holes: a first set of holes 7 and a second set of holes 6.

The first set of holes 7 is made up by at least two pairs of through holes 7, each pair of them being located on a different side of the central part 8 of the band 4, for example at 1.5 cm from the midline of the elongated band 4. In the exemplary embodiment shown in FIG. 3, the through holes 7 of each pair of the first set of holes 7 are aligned in the direction along the width of the band 4, although according to another embodiment, they could be aligned in the direction along the length of the band 4. First threads 70 passes through the first set of holes 7, in particular, each first thread 70 goes through the two holes 7 of each of said pairs, in such a way that both ends of said first thread 70 goes out from each hole 7. As it will be explained later with reference to FIG. 4, the first set of holes 7 and the first threads 70 are exclusively meant for loosening the band 4 following the placement of the band 4 and the conclusion of the operation. To sum up, there is at least one thread 70 on either side of the central part 8 of the band 4, but from outside it can appear that there are two threads 70, because the ends of said thread 70 are the ones that comes out from the holes 7.

The second set of holes 6 is located closer to the distal ends of the band 4 than the first set of holes 7 and is made up by several pairs of through holes 6 disposed in the direction along the length of the band 4, wherein the holes 6 of a same pair are aligned along the width of said band 4. As it happens in the first set of holes 7, second threads 60 pass through the second set of holes 6. The second set of holes 6 and the second threads 60 are exclusively meant for tightening the band 4.

In addition, the band 4 gets narrower at its both ends and terminate in filiform elements 5 which can be threaded through the hole 3 of the needle 1 of the band positioning device.

As shown in FIG. 3, the elongated band 4 includes, on either side of the midline of the band 4, two pairs of holes 7 belonging to the first set of holes 7 close to the central part 8 of the band 4, and three pairs of holes 6 belonging to the second set of holes 6 close to the end of the band 4, and a first set of threads 70 and second set of threads 60 passing through each pair of the holes 7 and 6, respectively. In this exemplary embodiment, both ends of each thread (60 or 70) that pass through a respective pair of holes 7 and 6 are joined by a joining element such as an adhesive tape or a piece of strip made of a suitable surgical material, or just tied by a knot, forming a loop. This configuration in loops keeps the threads always attached to the band 4.

The elongated band 4, which includes the first threads 70 and second threads 60 passing through the first and second sets of holes 7 and 6, respectively, is placed by the surgeon in the proximal urethra of the patient via a small incision in the anterior vaginal wall and two small incisions in the hypogastrium (the suprapubic area) of the patient.

The band 4 can be introduced and placed in the proximal urethra from the hypogastrium to vagina or from the vagina to the hypogastrium.

Figure 4:
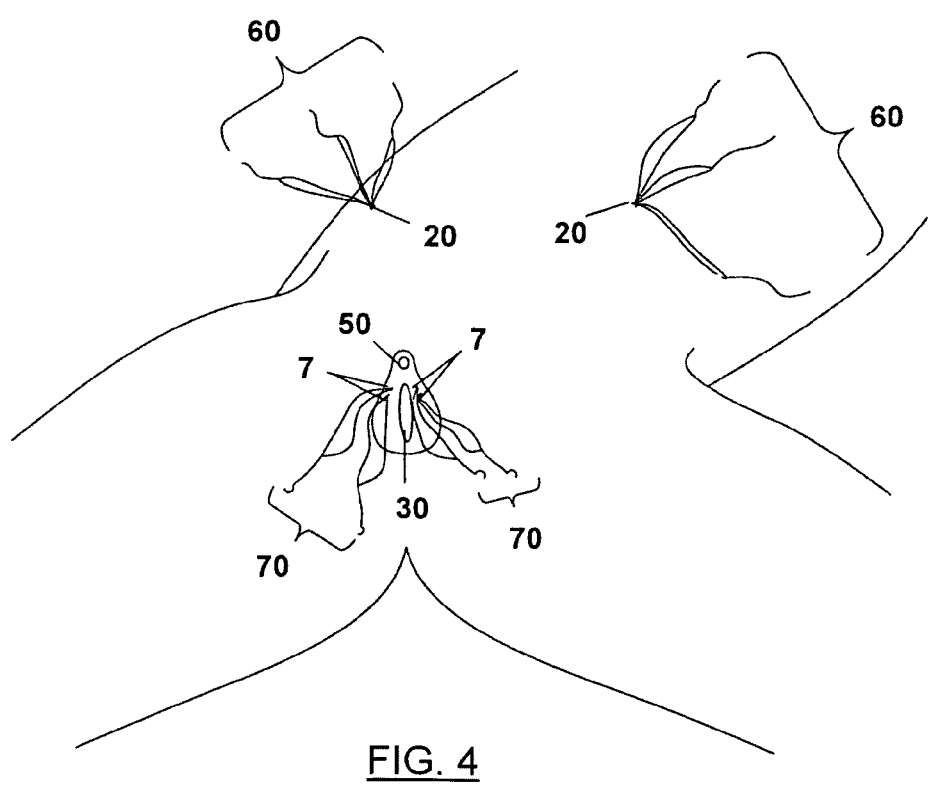
FIG. 4 is an illustrative representation of the process of tightening/loosening the band in a post-operative procedure.

For example, with reference to FIG. 4, the surgeon introduces the needle (tunneller) 1 of the band 4 positioning device (shown in FIG. 1) in one of the suprapubic incisions 20 and passes the tunneller 1 to the vagina 30. Then, the surgeon connects the band (mesh) 4, for example by threading the filiform elements 5, to the tunneller and pulls up the tunneller having in that way one branch of the mesh 4 in the suprapubic area. Afterwards, the surgeon passes again the tunneller through the other suprapubic incision 20 to the other side of the vagina 30. Again, the surgeon connects this to the mesh and pulls up. As a result, the mesh will be placed below the urethra 50 and the two ends of the band 4 project out through the suprapubic incisions 20.

Thus, the band 4 goes from one incision 20 in the hypogastrium to the other incision 20 in the hypogastrium passing below the urethra 50, as it is shown in FIG. 4. In this position, the two branches in the band 4 are distinguishable, as they are divided by the central part 8 of the band 4, that is, the urethra area 8.

Figure 5:
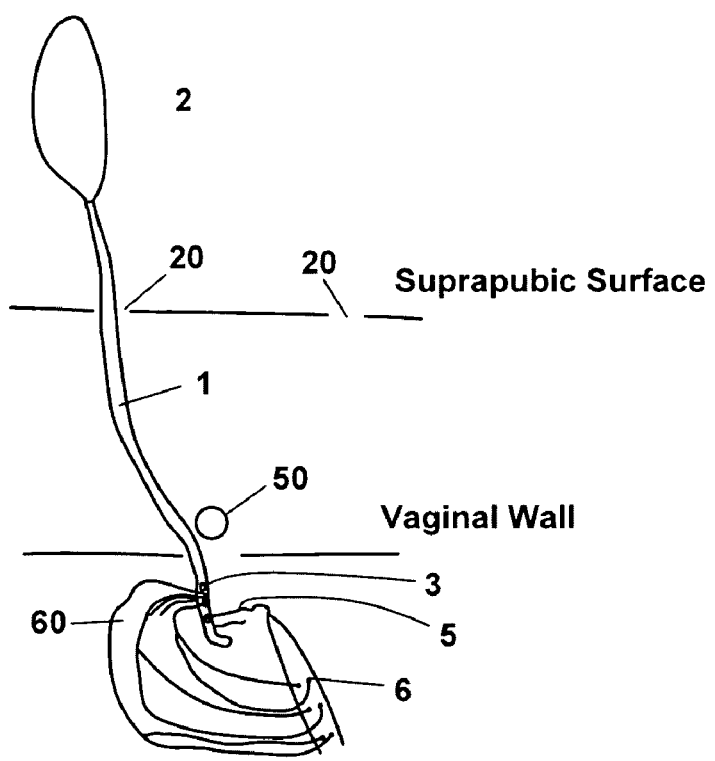
FIGS. 5 and 6 illustrate the band of FIGS. 3 and 4 being passed between the suprapubic surface and the vaginal wall of the patient.
Figure 6:
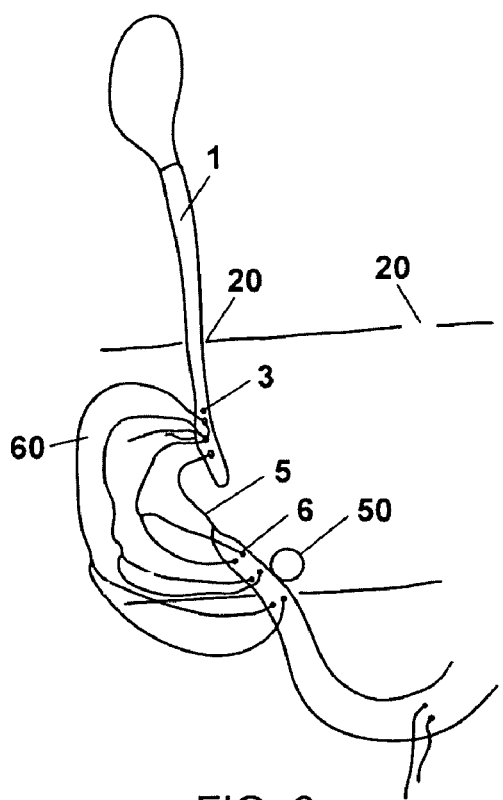

FIG. 5 shows the mesh being passed from the vagina to a suprapubic surface. As shown, the tunneller 1 can have one, two, or three holes. The thread to pull to pass the mesh is the filiform element 5 at the end of the mesh. FIG. 6 shows another point at which the mesh 4 is being passed from the vagina to the suprapubic surface.

Figure 7:
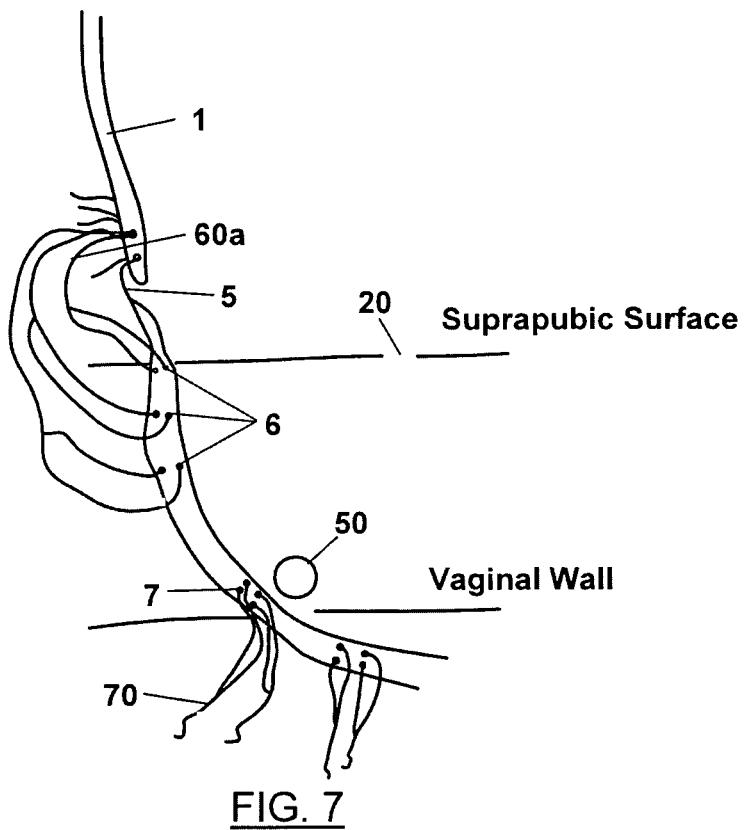
FIGS. 7-10 illustrate the band shown in FIGS. 3 and 4 placed in patients with varying body masses.

FIG. 7 shows a branch of the mesh 4 being passed from the vagina to the suprapubic surface, wherein the patient is neither too obese nor too thin. As shown, one second thread 60a is out of the skin.

Figure 8:
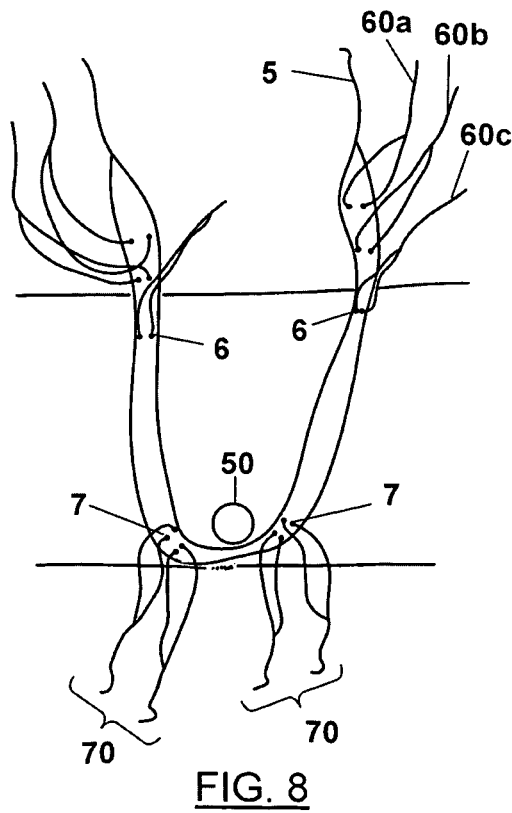

FIG. 8 shows the band when both branches have been passed between the vagina and the suprapubic surface, wherein the patient is a thin patient. Two second threads 60a and 60b on each side are externalized, i.e., out of the skin. Therefore, the tightening adjustment will have to be done with only one second thread 60c on each side.

Figure 9:
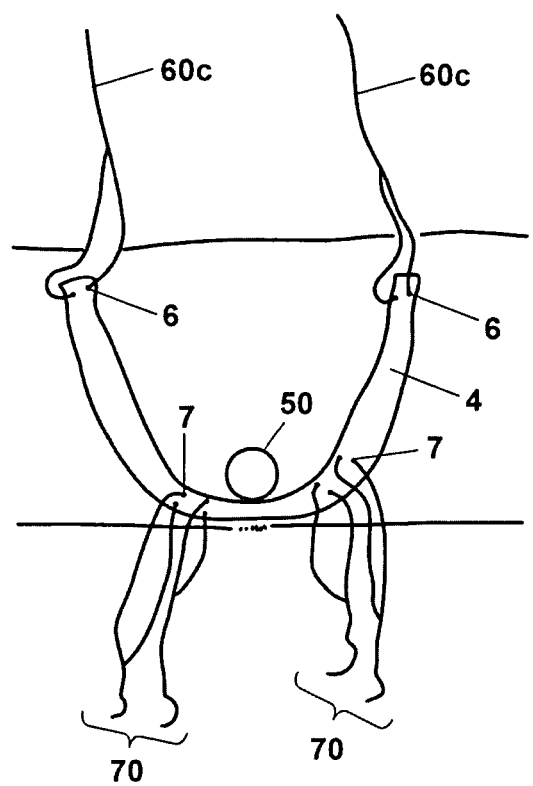

FIG. 9 shows the band placed in the thin patient as shown in FIG. 8, but the passing thread (filiform element 5) and the extra (redundant mesh) protruding from the skin have been cut and removed. The first threads 70 are coming out lateral to the vaginal incision. They can also be extracted through the incision.

Figure 10:
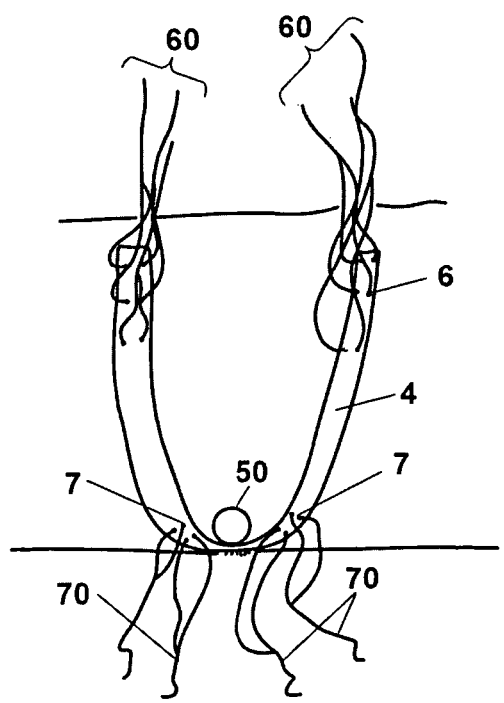

FIG. 10 shows the band placed in an obese patient. As shown, all the second threads 60 are inside. The passing thread (filiform element 5) and the extra (redundant) mesh have been cut and removed. The tightening adjustment of the mesh 4 will be done with all the second threads 60, pulling from all at the same time.

In the exemplary embodiments shown in FIGS. 3 and 4, the band 4 is longer than the final length needed, the excess band has to be cut and removed to avoid infections (the final length of the band 4 depends on the distance from the urethra 50 to the skin of the hypogastrium incisions 20 in the patient). The inferior part of the three second threads 60 (superior threads) which are threaded in the holes of the band 4 will be usually located under the skin surface but in thin patients, one or even two of the second threads 60 can go out from the skin. As such, these will have to be cut. The adjustment in this case (thin patients) will be made with the first threads 70 and the leftover second threads 60. With obese patients, the adjustment will be performed with the whole second threads 60 on each side and with the first threads 70.

It is important that the surgeon makes all the first threads 70 of the first set of holes 7 come out to the exterior of the patient's body. This is made possible by vaginal incision or passing the first threads 70, with a needle 1, laterally to the incision, leaving the left first threads 70 to the left side and the right first threads 70 to the right side. All the second threads 60 of the second set of holes 6 (six threads in the exemplary embodiment shown in FIG. 4) also have to come out to the exterior of the patient's body through the incisions 20 of the hypogastrium, leaving three second threads 60 on each side.

During surgery the surgeon does not need to use the first threads 70 or the second threads 60. The surgeon places the band 4 manually, and pulls the band 4 up or down. When the surgeon thinks that the band 4 is in a correct position, the operation is finished and the surgeon closes the incisions. The surgeon does not fix the first threads 70 or the second threads 60 to the skin. The mesh 4 is fixed by itself due to its shape, it produces a very big adherence to the tissues around, a very big resistance to go down.

In the days following the surgery, the doctors can test if the patient is continent or not, for example, by filling the bladder with certain amount of saline solution and asking the patient to cough in supine and standing positions, and by controlling the uroflowmetry and post-void residual urine measurement.

If it is inferred that the patient is still incontinent, it means that the tension applied to the band 4 is not enough and therefore, it must be increased. With the band 4 according to an exemplary embodiment of the invention, this correction of the tension can be done during the postoperative days with the patient being awake. To tighten the band 4, it is just needed to pull up the second threads 60 that come out from the incisions 20 in the hypogastrium (suprapubic area). If the patient is overweight, there will still be three second threads 60 on each side, but if she is thin, there might be just one second thread 60 on each side.

On the contrary, if it is inferred that the patient suffers obstruction in the urethra 50, it means that the urethra 50 is tilted upwards and that the tension of the band 4 must be decreased. To loosen the band 4, the first threads 70 which come out from the anterior vaginal walls are pulled, because in that way, the lower part of the band 4 will go downwards, that is, toward the vagina 30, and the urethra 50 and thus will not suffer any strangulation due to its inclination or tilting.

Therefore, several adjustments of the tension of the band 4 can be carried out during the postoperative days with the patient awake, tightening the band 4 pulling upward the second threads 60 that come out from both incisions 20 of the hypogastrium, if the patient is still incontinent, or loosening the band 4 pulling the first threads 70 that come out from the open anterior vaginal walls if the urethra 50 of the patient is obstructed. Moreover, adjusting the tension of the band 4 preferably does not require forming folds in the band 4 or loosening folds 4 in the band, which is painful for the patient.

Once the results of the tests of the patient proves that she is continent and that she is not obstructed, all the first threads 70 and the second threads 60 are removed from the patient's body by just cutting a branch of the loop and pulling the other branch.

It must be mentioned that in the band 4 which has been previously disclosed, the first set of holes 7 can exclusively be used for loosening the band 4, whereas the second set of holes 6 can exclusively be used for tightening the band 4.

All the first and second holes 7 and 6 can be in the form of perforations specifically made in the band 4, close to the central part 8 of the band 4 and close to the ends of said band 4, respectively.

However, in an alternative embodiment, if the band 4 is made of fabric of mesh, the reticle of the mesh itself provides holes in those areas of the band 4 through which the first and second threads 60 can pass through. In such an embodiment, the first threads 70 and the second threads 60 are passed through the gaps in the mesh itself (1) in equivalent positions to those of the holes 7 and 6, respectively. In this embodiment, the threads 70 and 60 are previously attached to the mesh 4, without this operation having to be performed immediately prior to the surgical intervention.

In another exemplary embodiment, the band 4 is narrower at its both ends and ends with a filiform element (a thread) 5 that will allow, once passed through a hole 3 of the needle 1 of the positioning device, to drag the band 4 from the vagina 30 to the hypogastrium or vice versa. The rest of the threads, that is, three second threads 60 up and two first threads 70 down on each side are for tightening and for loosening the band 4 after the surgery, with the patient awake. The second threads 60 (the superior ones) need to be passed through a hole 3 of the needle 1 of the positioning device to make them come out to the exterior of the patient's body. They can pass through the same hole 3 of the needle 1 used with the filiform element 5 that drags the band 4 or through another hole of the needle 1 of the positioning device.

In another exemplary embodiment, each first thread 70 is provided with a needle at its end and with this needle, it is extracted through the open vaginal wall to the exterior. The first thread 70 can also be extracted directly through the incision made in the vaginal wall, keeping all the first threads 70 in the middle, instead of each group on each side.

In yet another alternative embodiment, the mesh (band) 4 is enveloped in a plastic and there is a tractor thread for passing the band 4 and another three second threads 60 for tightening. When the plastic envelope is removed by cutting the superior part of the plastic envelope, the three second threads 60 or tractor threads are left at each side, and when the excess band 4 is cut, depending on the obesity of the patient, one, two or three second threads 60 are left for tightening later.

Further, the steps of placing the band 4 in the surgery are as follows:

a) The tunneller 1 (of the positioning device shown in FIG. 1) passes from one incision 20 in the suprapubic area to the vagina 30.

b) The band 4 is connected to the positioning device, and this can be done in several ways, e.g., through a thread that has been passed through the band 4, passing through the band 4 directly, or by a plastic envelope.

c) The positioning device is dragged upward to have one branch of the band 4 in the suprapubic area.

d) Then, from the other suprapubic incision 20, the positioning device is passed to the vagina 30, the band 4 is connected to the positioning device and dragged upward. Therefore, the band 4 forms an arc, wherein the middle part of the band 4 is below the urethra 50 and both ends are externalized from the suprapubic incisions 20.

Thereafter, the band 4 is left in the patient's body by the surgeon without tension or with a minimum tension, and preferably without folds. The band 4 itself is kept fixed in its position due to the form of the threads which make up the mesh 4 itself. The mesh threads have an oblique direction downward and so avoid that the mesh slide, which is also a problem with related art meshes used for urinary incontinence.

After the post-operative procedure (when the patient comes back home with all the first threads 70 and second threads 60 removed), the urethra 50 stays in the desired position due to the affixed mesh 4. When the patient coughs or makes some physical efforts, the urethra 50 will not go downward because it will bump into the mesh 4 that acts as a support. The mesh 4 is supported because the mesh threads have a great resistance with respect to the tissues going downward.

As will be understood, the configuration adopted by the system components permit that, from the use of the latter, a series of advantages are derived, from which, those summarized below stand out as most important.

The procedure is less aggressive, by virtue of the needle used having a smaller caliber. The product is less expensive, since plastic covers are eliminated in certain exemplary embodiments, simplifying the joining of the mesh to the thread passer, with the same needle serving for both approach directions.

In addition, it is now possible to achieve what had not been attained up to now, and which consists of the modification of the tension given to the sling with the patient awake, therefore correcting any dysfunction (obstruction or incontinence) produced in the prior operation.

While this invention has been particularly shown and described with reference to exemplary embodiments thereof, it will be understood by those of ordinary skill in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. A system for the treatment of stress urinary incontinence by returning the vesical neck and the urethra to a correct position with the use of a band positioned beneath the urethra and tightened to a desired position, comprising:

a band positioning device, comprising a handle, a needle, and a hole at or near a distal end of the needle;

an elongated band, comprising a urethral area at a central part of the band, the band comprising a first set of holes, one of the first set of holes located on one side of the central part and another of the first set of holes located on the other side of the central part along the length of the band;

first threads passing through the first set of holes and configured to permit loosening of the band following the placement of the band and the conclusion of the operation; and a second set of holes located closer to distal ends of the band than the first set of holes, and second threads passing through the second set of holes and configured to permit tightening of the band following the placement of the band and the conclusion of the operation, wherein the band and the first threads are assembled and configured to permit loosening of the band following the placement of the band and the conclusion of the operation without the band first comprising folds prior to loosening.

2. The system according to claim 1, wherein the first threads and the second threads are structured and located so that, following the placement of the band on a aponeurosis of the rectus level and periurethral level and the conclusion of the operation, the first threads and the second threads are accessible outside the corresponding lines of vaginal and retropubic sutures for post-operative adjustment of the band.

3. The system according to claim 1, wherein the band narrows at both ends, terminating in filiform elements configured to be threaded through the hole of the needle during the operation.

4. The system according to claim 1, wherein the hole in the needle is an elongated hole extending in a longitudinal direction of the needle.

5. The system according to claim 1, wherein the band has a mesh structure.

6. The system according to claim 1, wherein the center part of the band is a urethral apposition area and one of the first set of holes is positioned at a distance of approximately 1 and 2 cm from the center part of the band and the another of the first set of holes is positioned at a distance of approximately 1 and 2 cm from the center part of the band on an opposite side of the central part of the band.

7. A system for the treatment of stress urinary incontinence by returning the vesical neck and the urethra to a correct position with the use of a band positioned beneath the urethra and tightened to a desired position, comprising:

a band positioning device, comprising a handle, a needle, and a hole at or near a distal end of the needle;

an elongated band, comprising a urethral area at a central part of the band, the band comprising a first set of holes, one of the first set of holes located on one side of the central part and another of the first set of holes located on the other side of the central part along the length of the band;

first threads passing through the first set of holes and configured to permit loosening of the band following the placement of the band and the conclusion of the operation; and a second set of holes located closer to distal ends of the band than the first set of holes, and second threads passing through the second set of holes and configured to permit tightening of the band following the placement of the band and the conclusion of the operation, wherein the system is constructed so as to provide post-operative adjustment of the band without folds in the band.

8. The system according to claim 7, wherein the adjustment includes loosening of the band constructed so as to provide post-operative adjustment of the band without folds in the band.

9. A system for the treatment of stress urinary incontinence by returning the vesical neck and the urethra to a correct position with the use of a band positioned beneath the urethra and tightened to a desired position, comprising:

a band positioning device, comprising a handle, a needle, and a hole at or near a distal end of the needle;

an elongated band, comprising a urethral area at a central part of the band; and means for loosening and tightening the band following the placement of the band and the conclusion of the operation, wherein the means for loosening and tightening the band following the placement of the band and the conclusion of the operation does not comprise folds in the band.

10. A method of post-operatively adjusting the vesical neck and the urethra to a correct position with the use of a band positioned beneath the urethra and tightened to a desired position, the method comprising:

if the band needs to be loosened, pulling on first threads that pass through a first set of holes in the band located on at least one side of a central part of the band along the length of the band; and if the band needs to be tightened, pulling on second threads that pass through a second set of holes in the band located closer to distal ends of the band than the first set of holes, wherein the pulling on the first threads to loosen the band comprises pulling on the first threads following placement of the band and conclusion of the operation without the band first comprising folds prior to the pulling on the first threads.

* * * * *